(12) United States Patent
Kwon et al.

(10) Patent No.: US 12,167,834 B2
(45) Date of Patent: Dec. 17, 2024

(54) COLON LINEARIZING DEVICE, COLON LINEARIZING SYSTEM INCLUDING THE SAME AND METHOD OF MANUFACTURING THE COLON LINEARIZING DEVICE

(71) Applicants: KOREA ADVANCED INSTITUTE OF SCIENCE AND TECHNOLOGY, Daejeon (KR); ROEN Surgical, Inc., Daejeon (KR)

(72) Inventors: Dong Soo Kwon, Daejeon (KR); Han Soul Kim, Daejeon (KR); Jae Min You, Daejeon (KR); Joon Hwan Kim, Daejeon (KR); Duk Sang Kim, Daejeon (KR)

(73) Assignees: KOREA ADVANCED INSTITUTE OF SCIENCE AND TECHNOLOGY, Daejeon (KR); ROEN Surgical, Inc., Daejeon (KR)

( * ) Notice: Subject to any disclaimer, the term of this patent is extended or adjusted under 35 U.S.C. 154(b) by 411 days.

(21) Appl. No.: 17/616,990

(22) PCT Filed: Mar. 31, 2021

(86) PCT No.: PCT/KR2021/003992
§ 371 (c)(1),
(2) Date: Dec. 6, 2021

(87) PCT Pub. No.: WO2022/169024
PCT Pub. Date: Aug. 11, 2022

(65) Prior Publication Data
US 2022/0240764 A1    Aug. 4, 2022

(51) Int. Cl.
*A61B 1/00*    (2006.01)
*A61B 1/31*    (2006.01)
(Continued)

(52) U.S. Cl.
CPC ...... *A61B 1/00154* (2013.01); *A61B 1/00066* (2013.01); *A61B 1/00124* (2013.01);
(Continued)

(58) Field of Classification Search
CPC ............ A61B 1/00154; A61B 1/00066; A61B 1/00124; A61B 1/0016; A61B 1/31;
(Continued)

(56) References Cited

U.S. PATENT DOCUMENTS 3,865,666 A * 2/1975 Shoney ............. B29C 45/14336
264/254
5,243,967 A * 9/1993 Hibino ..................... A61B 1/12
600/137
(Continued)

FOREIGN PATENT DOCUMENTS

JP    2001315636    11/2001
JP    2006026343    2/2006
(Continued)

*Primary Examiner* — Timothy J Neal
*Assistant Examiner* — James Edward Boice
(74) *Attorney, Agent, or Firm* — JCIPRNET

(57) ABSTRACT

A colon linearizing device installed in an endoscope to linearize a colon by performing translation and expansion motions in the colon may include a ring-shaped proximal member installed to surround an outer circumferential surface of an insertion tube of an endoscope, a fixed end secured to the insertion tube, a ring-shaped distal member positioned between the proximal member and the fixed end (Continued)

and movably installed along a longitudinal direction of the insertion tube, and an elastic member connected between the fixed end and the distal member.

12 Claims, 8 Drawing Sheets

(51) Int. Cl.
*A61M 25/10* (2013.01)
*B29C 45/00* (2006.01)
*B29K 83/00* (2006.01)
*B29L 31/00* (2006.01)

(52) U.S. Cl.
CPC ............ *A61B 1/0016* (2013.01); *A61B 1/31* (2013.01); *A61M 25/1029* (2013.01); *B29C 45/0053* (2013.01); *B29K 2083/00* (2013.01); *B29L 2031/7546* (2013.01)

(58) Field of Classification Search
CPC .......... A61M 25/1029; A61M 25/1027; B29C 45/0053; B29K 2083/00; B29L 2031/7546; B29L 2031/754
USPC ................................................. 600/115, 116
See application file for complete search history.

(56) References Cited

U.S. PATENT DOCUMENTS

| | | | | |
|---|---|---|---|---|
| 5,707,355 A | * | 1/1998 | Zimmon | ............ A61M 16/0481 604/500 |
| 2013/0090527 A1 | | 4/2013 | Axon | |
| 2016/0249900 A1 | * | 9/2016 | Aoki | ................. A61M 25/0155 606/130 |

FOREIGN PATENT DOCUMENTS

| | | | |
|---|---|---|---|
| JP | 2006026372 | | 2/2006 |
| JP | 2006141935 | | 6/2006 |
| JP | 2006141935 A | * | 6/2006 |
| JP | 2007268137 | | 10/2007 |
| JP | 2009240713 | | 10/2009 |
| JP | 4487317 | | 6/2010 |
| JP | 2014157292 | | 8/2014 |
| JP | 2014200324 | | 10/2014 |
| JP | 2014228658 | | 12/2014 |
| JP | 2018005077 | | 1/2018 |
| KR | 20010030931 | | 4/2001 |
| KR | 20150051441 | | 5/2015 |

* cited by examiner

COLON LINEARIZING DEVICE, COLON LINEARIZING SYSTEM INCLUDING THE SAME AND METHOD OF MANUFACTURING THE COLON LINEARIZING DEVICE

CROSS-REFERENCE TO RELATED APPLICATION

This application is a 371 of international application of PCT application serial no. PCT/KR2021/003992, filed on Mar. 31, 2021, which claims the priority benefit of Korean application no. 10-2021-0015622, filed on Feb. 3, 2021. The entirety of each of the above-mentioned patent applications is hereby incorporated by reference herein and made a part of this specification.

TECHNICAL FIELD

The following description relates to a colon linearizing device, a system including the same, and a method of manufacturing the colon linearizing device.

BACKGROUND ART

The large intestine is largely divided into fixed and non-fixed parts, and the S-shaped colon and the transverse colon are non-fixed parts. It is difficult to insert an endoscope into a non-fixed part because the non-fixed part moves together with the movement of the endoscope. Therefore, for successful insertion and driving of the endoscope, a skillful insertion technique of a specialist who is able to linearize and shorten the colon is needed. However, the technique requires a long time for beginners to learn due to a high level of difficulty, and is limitedly implemented in endoscopic robotic surgery by remote control. Therefore, there is a need for a study on a safe and efficient method to help with the insertion and driving of the endoscope in endoscopic robotic surgery.

Various methods for driving in the large intestine using self-propulsion have been proposed, but are insufficient to apply to a clinical environment since the structure and volume of a device greatly hinders securing a surgical tool channel and a service channel. For example, there is a method of driving a system by attaching it to an outer side of an endoscope. However, there is an issue that the pressure used to operate the proposed system exceeds the pressure (e.g., 7.6 kPa) normally allowed inside the large intestine.

The above description is information the inventor(s) acquired during the course of conceiving the present disclosure, or already possessed at the time, and is not necessarily art publicly known before the present application was filed.

DISCLOSURE OF INVENTION

Technical Goals

Example embodiments provide a colon linearizing device capable of driving in a colon by linearizing a colon and inserting a surgical tool such as an endoscope into the colon, a colon linearizing system including the same, and a method of manufacturing the colon linearizing device.

Technical Solutions

According to an aspect, there is provided a colon linearizing device installed in an endoscope to linearize a colon by performing translation and expansion motions in the colon, the colon linearizing device including a ring-shaped proximal member installed to surround an outer circumferential surface of an insertion tube of an endoscope, a fixed end secured to the insertion tube, a ring-shaped distal member positioned between the proximal member and the fixed end and movably installed along a longitudinal direction of the insertion tube, and an elastic member connected between the fixed end and the distal member.

The proximal member and the distal member may support an inside of the colon in an expanding state.

The elastic member may have an elastic restoring force that increases as the distal member approaches the proximal member.

The proximal member may include a proximal frame having a hollow for receiving the insertion tube, and a proximal balloon disposed with both ends in close contact with an outer circumferential surface of the proximal frame and formed of a flexible material.

The proximal frame may include a frame body, a balloon mount recessed from a side surface of the frame body such that the proximal balloon seated therein, and an air hole formed in the frame body to guide air introduced from an outside into a space between the frame body and the proximal balloon.

The proximal frame may further include a wire hole formed through the frame body.

According to an aspect, there is provided a colon linearizing system including the colon linearizing device, the colon linearizing system further including a translation drive device to translate the distal member, and an expansion drive device to expand the distal member or the proximal member by supplying air pressure to the distal member or the proximal member.

The translation drive device may translate the distal member to approach the proximal member by providing power to the distal member, and when the translation drive device does not provide power to the distal member, the distal member may be translated in a direction toward the fixed end by the elastic restoring force of the elastic member.

The translation drive device may include a base, a driving block capable of sliding relative to the base, a vertically moving block capable of sliding relative to the base and connected to the distal member, and an electromagnet module capable of magnetically coupling the driving block and the vertically moving block.

The electromagnet module may include a first magnetic body installed in any one of the driving block and the vertically moving block, and a second magnetic body installed in the other one of the driving block and the vertically moving block.

The translation drive device may further include a driving motor, and a drive shaft to rotate according to an operation of the driving motor and translate the driving block in a ball-screw manner.

The expansion drive device may include an air tube to supply air pressure to the distal member or the proximal member, an air pressure sensor to measure pressure in the air tube, and an air pressure controller to control the pressure in the air tube according to an input time and pressure conditions.

According to an aspect, there is provided a method of manufacturing the colon linearizing device, wherein at least one of the distal member and the proximal member may include a frame having a hollow for receiving the insertion tube, and a balloon disposed with both ends in close contact with an outer circumferential surface of the frame and formed of a flexible material, wherein the method may include manufacturing a mold corresponding to an outer shape of the balloon, forming the balloon by injecting silicone in the mold and curing the silicone, installing the balloon on a side surface of the frame and fixing both ends of the balloon to the side surface of the frame, and installing an air tube capable of supplying air from an outside to a space between the frame and the balloon.

The balloon may expand in a direction toward an outside diameter of the frame and may not expand in a direction toward an inside diameter of the frame.

Effects

According to example embodiments, a colon linearizing device, a colon linearizing system including the same, and a method of manufacturing the colon linearizing device may allow the colon linearizing device to drive in a colon by linearizing the colon and inserting a surgical tool such as an endoscope without learning a skillful insertion technique.

BEST MODE FOR CARRYING OUT THE INVENTION

Figure 1:
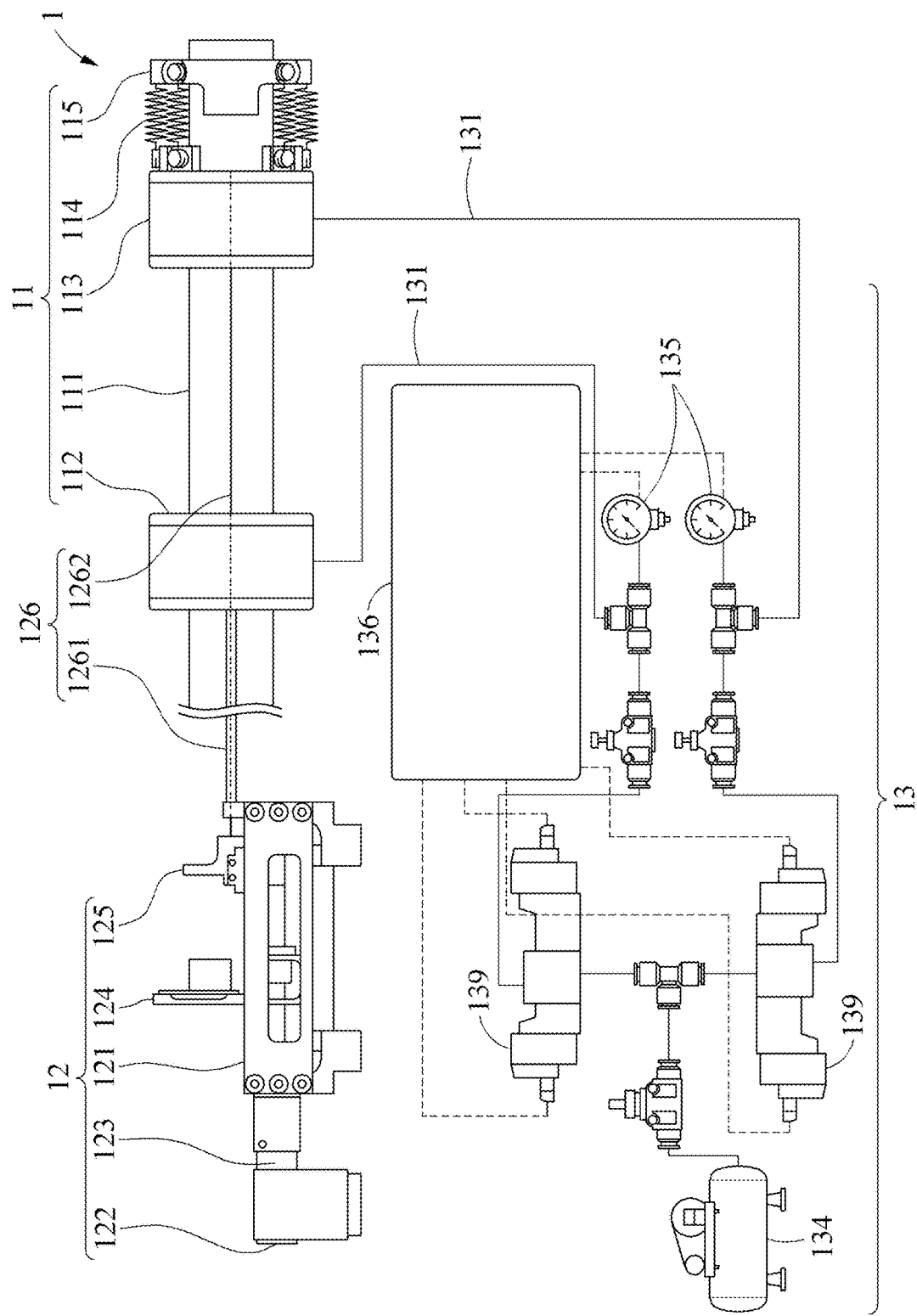
FIG. 1 is a view illustrating a colon linearizing system according to an example embodiment.

Hereinafter, example embodiments of the present disclosure will be described with reference to the accompanying drawings. Regarding the reference numerals assigned to the components in the drawings, it should be noted that the same components will be designated by the same reference numerals, wherever possible, even though they are shown in different drawings. Also, in the description of the example embodiments, detailed description of well-known related structures or functions will be omitted when it is deemed that such description will cause ambiguous interpretation of the present disclosure.

Also, in the description of the components, terms such as first, second, A, B, (a), (b) or the like may be used herein when describing components of the present disclosure. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the example embodiments described above and an element having a common function. Unless otherwise mentioned, the descriptions on the example embodiments may be applicable to the following example embodiments and thus, duplicated descriptions will be omitted for conciseness.

Figure 2:
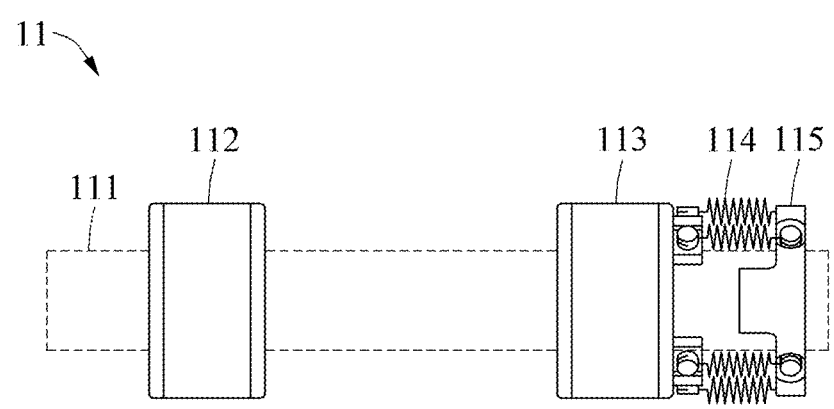
FIG. 2 is a view illustrating a colon linearizing device according to an example embodiment.
Figure 3:
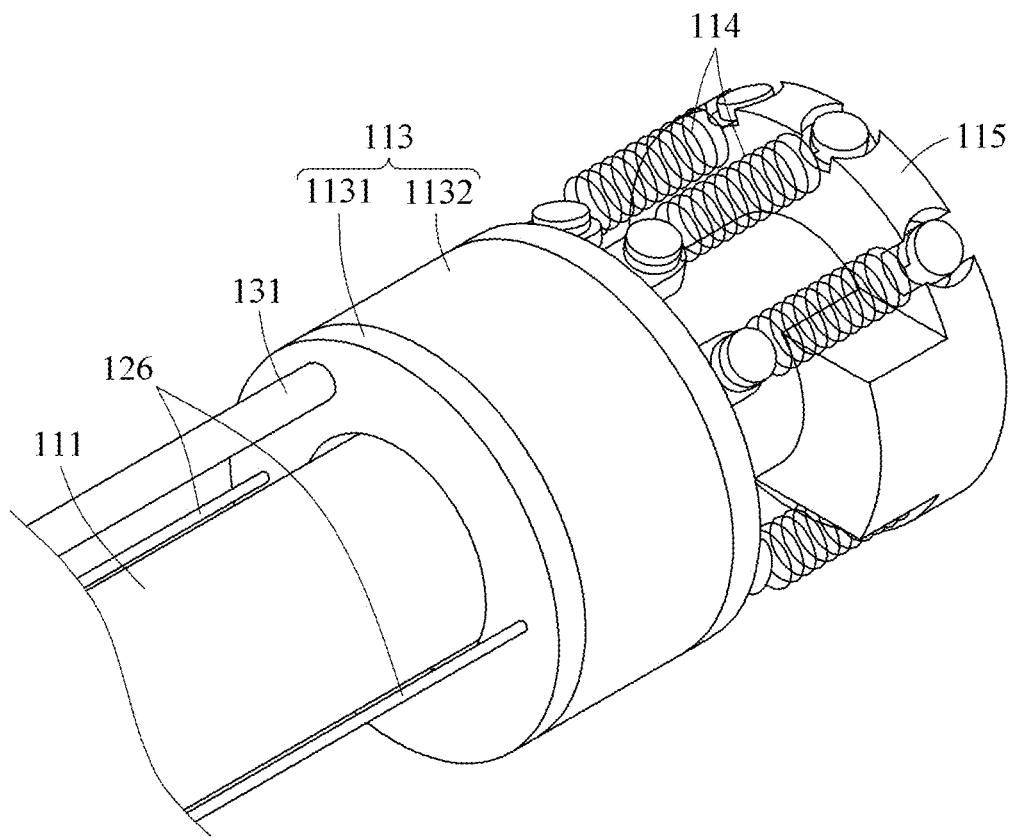
FIG. 3 is a perspective view of a portion of a colon linearizing device according to an example embodiment.

FIG. 1 is a view illustrating a colon linearizing system according to an example embodiment, FIG. 2 is a view illustrating a colon linearizing device according to an example embodiment, and FIG. 3 is a perspective view of a portion of the colon linearizing device according to an example embodiment.

Referring to FIGS. 1 to 3, a colon linearizing system 1 may effectively linearize a curved portion of a colon through translation and expansion motions of a colon linearizing device 11. When the colon is linearized, an insertion tube 111 of an endoscope may easily enter the colon. For example, the colon linearizing system 1 may include the colon linearizing device 11, a translation drive device 12, and an expansion drive device 13.

The colon linearizing device 11 may linearize the colon by expanding and translating while receiving the insertion tube 111 of the endoscope therein, and move a relative position of the colon with respect to the insertion tube 111 of the endoscope rearward (e.g., in a direction opposite to the insertion direction of the endoscope), thereby allowing the insertion tube 111 of the endoscope to easily pass through the curved portion of the colon. The colon linearizing device 11 may be about 90 mm in length. For example, the colon linearizing device 11 may include an insertion tube 111, a proximal member 112, a distal member 113, an elastic member 114, and a fixed end 115.

The insertion tube 111 may be a part of the endoscope to be inserted into a body of a patient, and may include a hollow channel therein to function as a withdrawal passage for a camera and/or various surgical tools (e.g., clamps, forceps, or baskets). For example, the insertion tube 111 may be about 15 mm in diameter. For example, an insertion tube 111 of a typical commercial endoscope may be used as the insertion tube 111. In other words, the colon linearizing device 11 may be provided to include the insertion tube 111 of the endoscope. Alternatively, a colon linearizing device 11 with an insertion tube 111 of a typical commercial endoscope mounted may be used.

The distal member 113 may surround an outer circumferential surface of the insertion tube 111 and be disposed movably relative to the insertion tube 111. The distal member 113 may be adjusted in distance to the proximal member 112 according to an operation of the translation drive device 12. The distal member 113 may pull the colon in a proximal direction (e.g., in the direction opposite to the insertion direction of the insertion tube 111) while contacting one part of the lining of the colon inside the colon by expanding its outer circumferential surface, according to an operation of the expansion drive device 13. The distal member 113 may include a distal frame 1131 and a distal balloon 1132.

The distal frame 1131 may slide on the insertion tube 111. For example, an inside diameter of the distal frame 1131 may be greater than an outside diameter of the insertion tube 111. The distal frame 1131 may be about 26 mm in outside diameter and about 16 mm in inside diameter. The inside diameter of the distal frame 1131 and the diameter of the insertion tube 111 may have a difference of about 1 mm.

The distal balloon 1132 may be disposed with both ends in close contact with an outer circumferential surface of the distal frame 1131 to prevent air leakage and formed of a flexible material to expand by air pressure. The distal balloon 1132 may be formed of biocompatible silicone (e.g., EcoFlex00-30, Smooth-On, Inc.) to minimize damage to the lining of the colon.

The proximal member 112 may be disposed to surround the outer circumferential surface of the insertion tube 111. The proximal member 112 may be spaced apart from the distal member 113 in a longitudinal direction of the insertion tube 111. For example, like the distal member 113, the proximal member 112 may be disposed movably relative to the insertion tube 111. Meanwhile, alternatively, the proximal member 112 may be fixed to the insertion tube 111. The proximal member 112 may support the colon while contacting one part of the lining of the colon inside the colon by expanding its outer circumferential surface according to the operation of the expansion drive device 13. In this state, when the expanded distal member 113 translates, the colon may be shortened and linearized. It may be understood that the distance of separation between the proximal member 112 and the distal member 113 is the distance by which the colon may be shortened through one repetitive operation. The proximal member 112 may include a proximal frame 1121 (see FIG. 8) and a proximal balloon 1122 (see FIG. 8).

Unless otherwise stated, the description of the distal frame 1131 and the distal balloon 1132 may apply to the proximal frame 1121 and the proximal balloon 1122.

The elastic member 114 may be connected between the distal member 113 and the fixed end 115. An elastic restoring force of the elastic member 114 may quickly shorten the distance between the distal member 113 and the fixed end 115, without using an active actuator, in a state in which the distal member 113 is away from the fixed end 115.

The fixed end 115 may be secured to one side of the insertion tube 111. For example, the fixed end 115 may be secured to a portion of the insertion tube 111 that is located opposite the proximal member 112 relative to the distal member 113.

The translation drive device 12 may drive a portion of the colon linearizing device 11 to perform a translation motion. The portion (e.g., the distal member 113) of the colon linearizing device 11 connected to the translation drive device 12 may move in one direction when current flows in an electromagnet module 1241, 1251 (see FIG. 5) of the translation drive device 12, and move in an opposite direction (e.g., in a distal direction) by the elastic restoring force of the elastic member 114 when current does not flow in the electromagnet module 1241, 1251. The translation drive device 12 may include a base 121, a driving motor 122, a drive shaft 123, a driving block 124, a vertically moving block 125, and a wire unit 126.

The base 121 may provide space in which the driving block 124 and the vertically moving block 125 may slide. For example, the base 121 may include a rail structure in which the driving block 124 and/or the vertically moving block 125 may slide.

The driving motor 122 may translate the driving block 124 by rotating the drive shaft 123. The driving motor 122 may be controlled by a microcontroller, allowing a user to adjust the rotation velocity and interval of the driving motor 122. The driving motor 122 may be, for example, a rotary servo motor.

The drive shaft 123 may be rotated in one direction or the other direction according to the rotation direction of the driving motor 122. According to the rotation direction and rotation angle of the driving motor 122, the rotation direction and rotation angle of the drive shaft 123 may be determined. For example, the drive shaft 123 may be a lead screw and a linear motion (LM) guide.

The driving block 124 may be installed slidably relative to the base 121 and coupled to the drive shaft 123 to translate on the base 121 according to the rotation direction and rotation angle of the drive shaft 123. For example, the driving block 124 and the drive shaft 123 may be connected in a ball-screw structure. In other words, the driving block 124 may translate forward (e.g., in a distal direction) or rearward (e.g., in a proximal direction) by means of the drive shaft 123. The driving block 124 may be selectively coupled to the vertically moving block 125 as described later, thereby translating the vertically moving block 125 rearward relative to the base 121.

The vertically moving block 125 may be installed slidably relative to the base 121 and connected to the distal member 113 to translate the distal member 113 forward (e.g., in a distal direction) or rearward (e.g., in a proximal direction). For example, the vertically moving block 125 may be connected to the distal member 113 by the medium of the wire unit 126. Meanwhile, since the distal member 113 is connected to the fixed end 115 by the elastic member 114, the elastic restoring force of the elastic member 114 may act on the vertically moving block 125 in a direction (e.g., in a distal direction) toward the fixed end 115, in a state in which no external force is applied.

Meanwhile, a first magnetic body 1241 (see FIG. 5) included in the driving block 124 and a second magnetic body 1251 (see FIG. 5) included in the vertically moving block 125 may be collectively referred to as the electromagnet module 1241, 1251. Any one of the first magnetic body 1241 and the second magnetic body 1251 (e.g., the first magnetic body 1241) may be formed of an electromagnet, and the other one magnetic body (e.g., the second magnetic body 1242) may be formed of a plate of a ferromagnetic material (e.g., iron, nickel, or cobalt), whereby a magnetic field may be generated according to whether current is applied. When current is applied to the electromagnet module 1241, 1251, the driving block 124 and the vertically moving block 125 may be magnetically coupled to slide integrally. Meanwhile, when no current is applied to the electromagnet module 1241, 1251, the vertically moving block 125 may be in a neutral state as being maximally translated in the distal direction by the elastic restoring force of the elastic member 114.

The wire unit 126 may connect the vertically moving block 125 and the colon linearizing device 11. For example, the wire unit 126 may include a sheath 1261 and a wire 1262.

The sheath 1261 may be a covering surrounding the wire 1262 and have greater rigidity than the wire 1262. The rigidity of the sheath 1261 may allow forming and maintaining an entry path inside the colon and prevent buckling. In addition, the sheath 1261 may prevent internal tissues of the colon or blood vessels from being damaged by friction with the wire 1262 that moves according to the translation driving. For example, the sheath 1261 may be disposed between the base 121 and the proximal member 112.

One end of the wire 1262 may be connected to the vertically moving block 125, and the other end of the wire 1262 may pass through the proximal member 112 and be connected to the distal member 113. When the vertically moving block 125 moves, the distal member 113 may be moved by a tension of the wire 1262. For example, the wire 1262 may be disposed between the vertically moving block 125 and the distal member 113.

The expansion drive device 13 may expand a portion of the colon linearizing device 11 by air pressure. For example, the expansion drive device 13 may include an air tube 131, an air compressor 134, an air pressure sensor 135, an air pressure controller 136, and a solenoid valve 139.

The air tube 131 may guide air from the air compressor 134 to the colon linearizing device 11.

The air compressor 134 may provide air pressure supplied through the air tube 131 by receiving air introduced from an outside and compressing the received air.

The air pressure sensor 135 may measure pressure in the air tube 131.

The air pressure controller 136 may control the pressure in the air tube 131 according to an input time and pressure conditions. For example, when the pressure measured by the air pressure sensor 135 exceeds a set pressure, the air pressure controller 136 may reduce air pressure provided to a balloon corresponding to the air pressure sensor 135, thereby preventing damage to the colon.

The solenoid valve 139 may be opened and closed by the air pressure controller 136. For example, the solenoid valve 139 may be a 5/3-way solenoid valve.

Figure 4:
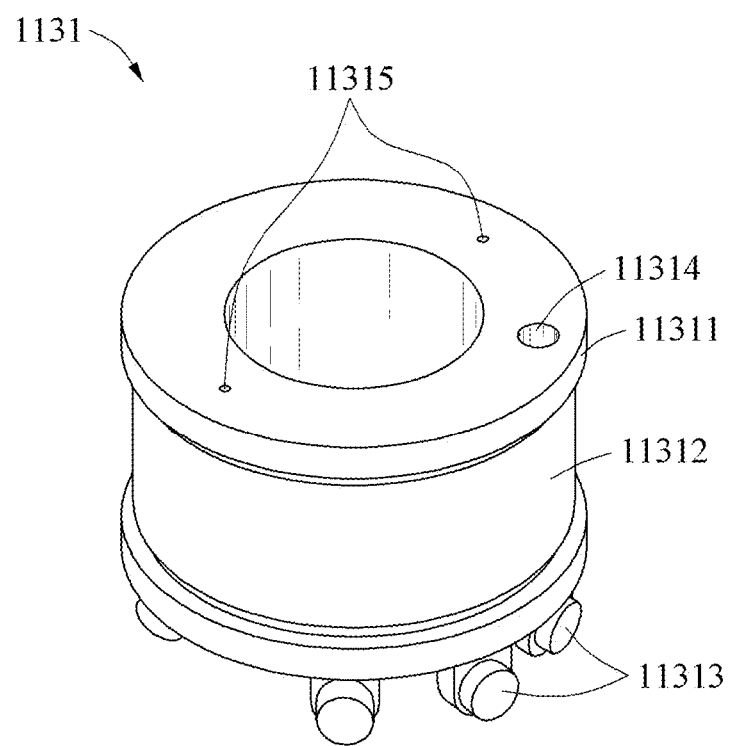
FIG. 4 is a perspective view of a distal frame according to an example embodiment.

FIG. 4 is a perspective view of a distal frame according to an example embodiment.

Referring to FIG. 4, the distal frame 1131 may include a frame body 11311, a balloon mount 11312, a connector 11313, an air hole 11314, and a wire hole 11315.

The frame body 11311 may have a hollow through which the insertion tube 111 passes, and a side surface on which the distal balloon 1132 is disposed. Flanges protruding outward may be formed at both ends of the side surface, so that the distal balloon 1132 may be more stably supported on the frame body 11311.

The balloon mount 11312 may be recessed from the side surface of the frame body 11311 and communicate with the air hole 11314.

The connector 11313 may be connected to the elastic member 114 to transmit an elastic force to the distal member 113.

The air hole 11314 may be formed in the frame body 11311 to guide air introduced from the outside into a space between the side surface of the distal frame 1131 and the distal balloon 1132.

The wire hole 11315 may be formed through the frame body 11311. For example, a plurality of wire holes 11315 may be formed radially at an equal interval, thereby preventing power transmitted from the translation drive device 12 to the frame body 11311 from being biased toward either side.

Although not shown, similar to the distal frame 1131, the proximal frame 1121 may include a frame body in which a proximal balloon is disposed, a balloon mount, an air hole, and a wire hole, and may not include a connector.

Figure 5:
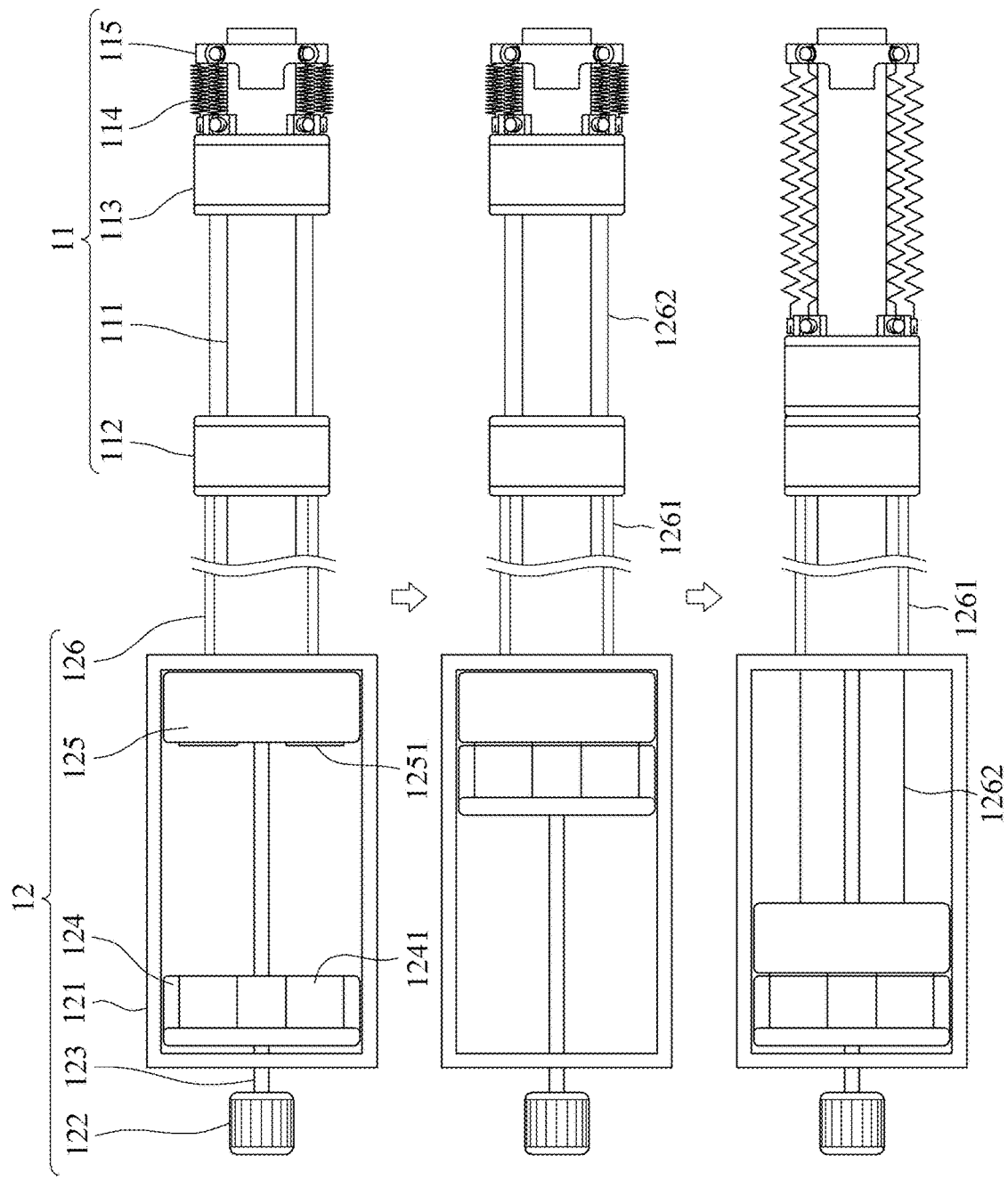
FIG. 5 is a view illustrating a driving process of a translation drive device according to an example embodiment.
Figure 6:
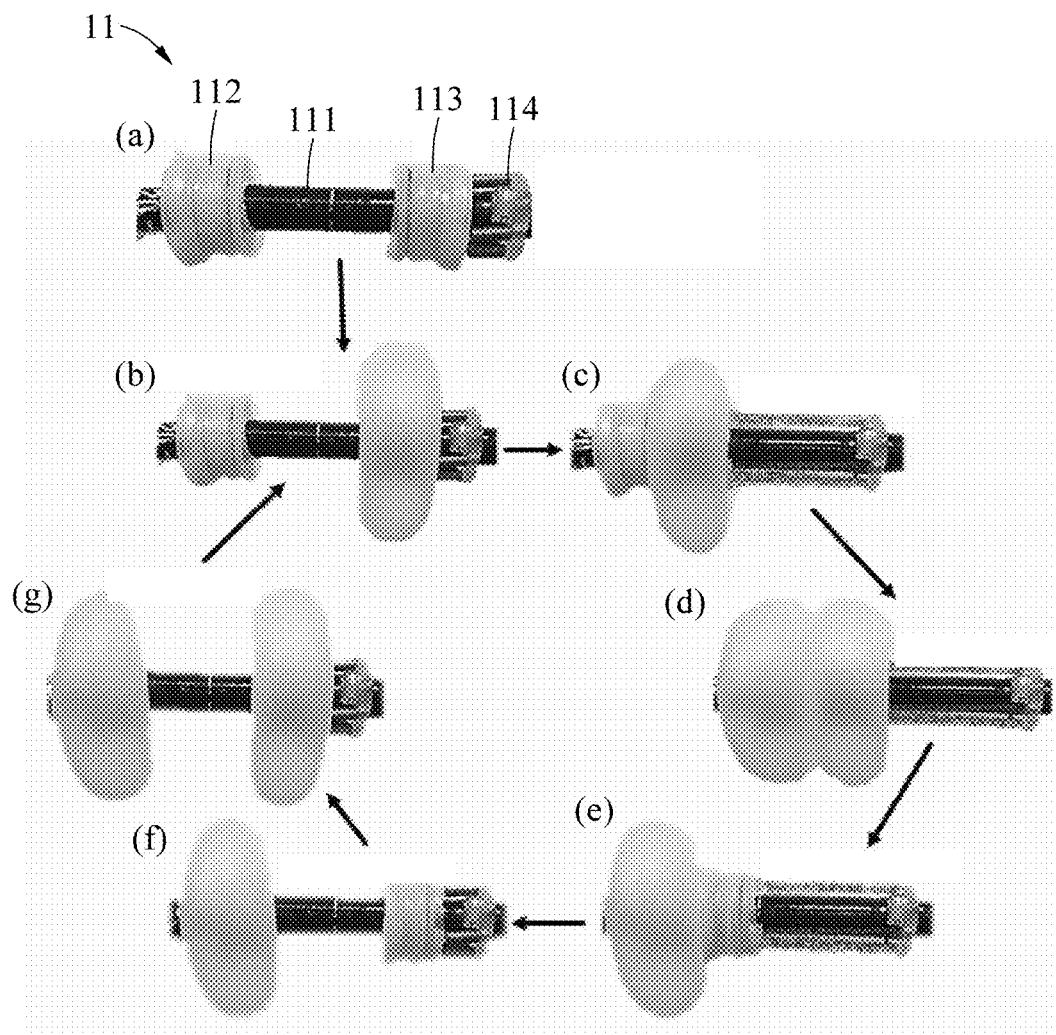
FIG. 6 is a view showing a translation and expansion driving process of a colon linearizing device according to an example embodiment.

FIG. 5 is a view illustrating a driving process of a translation drive device according to an example embodiment, and FIG. 6 is a view showing a translation and expansion driving process of a colon linearizing device according to an example embodiment.

Referring to FIGS. 5 and 6, first, the colon linearizing device 11 may access an entry of the colon through the anus. At this time, for easy entering, the distal member 113 and the proximal member 112 may be in an unexpanded state (a state (a) of FIG. 6).

In the state (a) of FIG. 6, the distal member 113 may expand by means of the expansion drive device 13 to support the lining of the colon (a state (b) of FIG. 6).

In the state (b) of FIG. 6, as sequentially shown in FIG. 5, (i) first, the shaft 123 may be rotated in one direction as the driving motor 122 is driven, such that the driving block 124 may move forward in a distal direction (e.g., in a direction toward the vertically moving block 125). (ii) Second, current may be applied to the electromagnet module 1241, 1251 in a state in which the driving block 124 and the vertically moving block 125 are in contact with each other, whereby the vertically moving block 125 may be magnetically coupled to the driving block 124 and move integrally with the driving block 124. (iii) Third, the driving block 124 may be rotated in the other direction as the driving motor 122 is driven in a reverse direction, such that the driving block 124 may move rearward in a proximal direction, and the vertically moving block 125 may move rearward together with the driving block 124, whereby the distal member 113 may be pulled toward the proximal member 112 by means of the wire 1262 (a state (c) of FIG. 6).

Accordingly, the distal member 113 may be moved to be closer to the proximal member 112 along the insertion tube 111 by the translation drive device 12 in an expanded state. Meanwhile, as the distal member 113 approaches the proximal member 112, the elastic member 114 may be greatly deformed, gradually increasing the elastic force.

In the state (c) of FIG. 6, as the proximal member 112 is expanded, both the distal member 113 and the proximal member 112 may support the colon in an expanded state (a state (d) of FIG. 6). At this time, the colon pulled by a support force of the distal member 113 may be supported together by the proximal member 112.

In the state (d) of FIG. 6, when the distal member 113 is contracted by discharging the air inside the distal member 113 by means of the expansion drive device 13, only the proximal member 112 may support the colon (a state (e) of FIG. 6).

In the state (e) of FIG. 6, when the distal member 113 is contracted and no current flows in the electromagnet module 1241, 1251, an attractive force that was in equilibrium with the elastic restoring force of the elastic member 114 may disappear, such that the distal member 113 may move in a contraction direction (e.g., a distal direction) of the elastic member 114 (a state (f) of FIG. 6).

In the state (f) of FIG. 6, the distal member 113 may expand again to support the colon (a state (g) of FIG. 6).

In the state (g) of FIG. 6, the proximal member 112 may be contracted. In this process, only the proximal member 112 may contract, returning to the state (b) of FIG. 6, and as described above with reference to FIG. 5, the distal member 113 may repeatedly pull and linearize the colon according to the translation driving principle using an electromagnet by supporting the colon in an expanded state.

Figure 7:
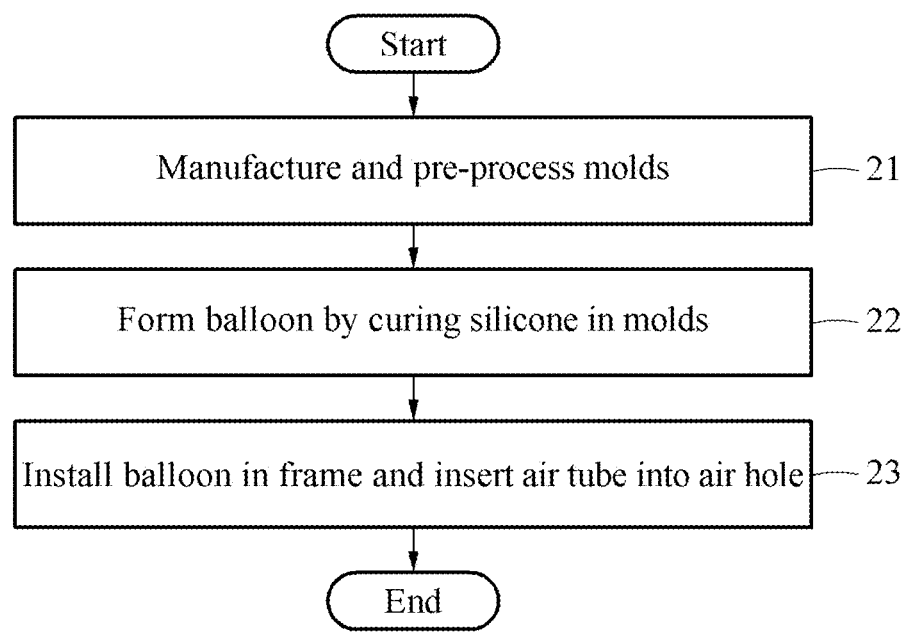
FIG. 7 is a flowchart illustrating a process of manufacturing a distal balloon and/or a proximal balloon according to an example embodiment.
Figure 8:
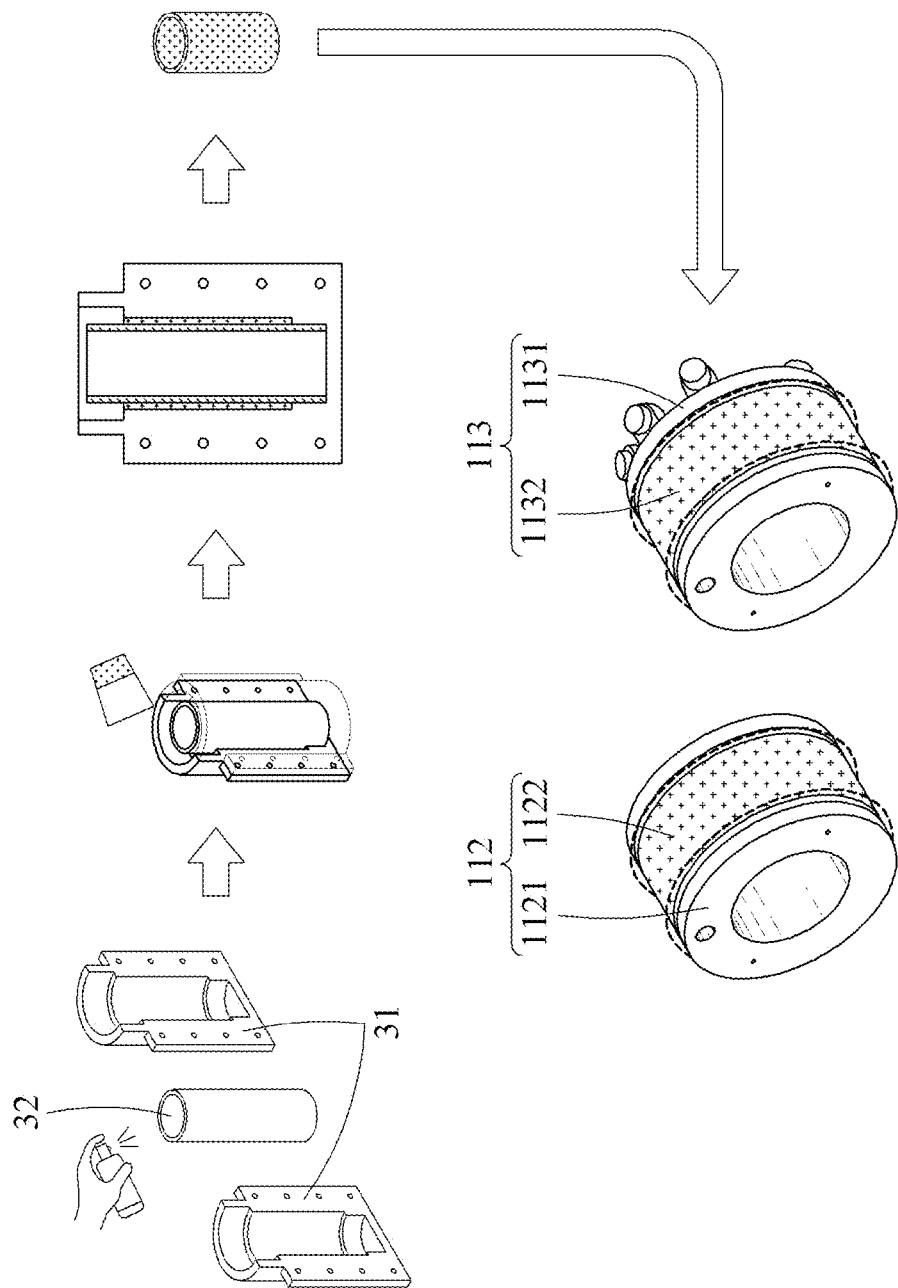
FIG. 8 is a view illustrating a process of manufacturing a distal member and/or a proximal member according to an example embodiment.

FIG. 7 is a flowchart illustrating a process of manufacturing a distal balloon and/or a proximal balloon according to an example embodiment, and FIG. 8 is a view illustrating a process of manufacturing a distal member and/or a proximal member according to an example embodiment.

Referring to FIGS. 7 and 8, a method of manufacturing the colon linearizing device 11 may include operation 21 of manufacturing and pre-processing molds 31 and 32, operation 22 of forming a balloon (e.g., the distal balloon 1132 and/or the proximal balloon 1122) by curing silicone in the molds 31 and 32, and operation 23 of installing the balloon in a frame (e.g., the distal frame 1131 and/or the proximal frame 1121) and inserting an air tube into an air hole.

In operation 21, the molds 31 and 32 may include an outer mold 31 shaping an outer surface of the balloons 1122 and 1132 and an inner mold 32 shaping an inner surface of the balloons 1122 and 1132. A difference between an inside diameter of the outer mold 31 and an outside diameter of the inner mold 32 may be a thickness of the balloons 1122 and 1132. For example, the molds 31 and 32 may be formed of aluminum metal. The molds 31 and 32 may be manufactured and pre-processed by applying a release agent (e.g., ER-200, Smooth-On, Inc.) thereto, so that the silicone may be easily removed from the molds.

In operation 22, the molds 31 and 32 may be assembled, and homogenized and air-free silicone may be poured into the assembled molds 31 and 32. The silicone curing process may be performed by leaving the silicone at room temperature for 30 minutes and at a temperature of about 100° C. in an oven for 30 minutes. A flexible material of a planar body having a shape of a side of a cylinder may be formed through operation 22, and may function as an expanding part in reality through operation 23.

In operation 23, the cured silicone may be separated from the molds 31 and 32, and the distal balloon 1132 and the proximal balloon 1122 may be installed in the distal frame 1131 and the proximal frame 1121, respectively. To prevent air from leaking from the distal balloon 1132 and the distal frame 1131 or the proximal balloon 1122 and the proximal frame 1121, both ends of the balloon may be tied with a string and restrained. By the structure described above, the balloon may be formed in a structure that expands only in an outward direction and does not expand in an inward direction. To prevent air leakage, a silicone adhesive (e.g., Sil-Poxy, Smooth-On, Inc.) may be used for sealing such that the distal balloon 1132 and the proximal balloon 1122 may not float from the distal frame 1131 and the proximal frame 1121.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

The invention claimed is:

1. A colon linearizing device installed in an endoscope to linearize a colon by performing translation and expansion motions in the colon, the colon linearizing device comprising:
a ring-shaped proximal member installed to surround an outer circumferential surface of an insertion tube of an endoscope;
a fixed end secured to the insertion tube;
a ring-shaped distal member positioned between the proximal member and the fixed end and movably installed along a longitudinal direction of the insertion tube;
an elastic member connected between the fixed end and the distal member;
a translation drive device to translate the distal member, wherein the translation drive device includes a base and a driving block; and
an expansion drive device to expand the distal member or the proximal member by supplying air pressure to the distal member or the proximal member, wherein the expansion drive device includes an air tube,
wherein, the translation drive device translates the distal member to approach the proximal member by providing power to the distal member, and
when the translation drive device does not provide power to the distal member, the distal member is translated in a direction toward the fixed end by the elastic restoring force of the elastic member.

2. The colon linearizing device of claim 1, wherein the proximal member and the distal member are capable of supporting an inside of the colon in an expanding state.

3. The colon linearizing device of claim 1, wherein the elastic member has an elastic restoring force that increases as the distal member approaches the proximal member.

4. The colon linearizing device of claim 1, wherein the proximal member comprises:
a proximal frame having a hollow for receiving the insertion tube; and
a proximal balloon disposed with both ends in close contact with an outer circumferential surface of the proximal frame and formed of a flexible material.

5. The colon linearizing device of claim 4, wherein the proximal frame comprises:
a frame body;
a balloon mount recessed from a side surface of the frame body such that the proximal balloon seated therein; and
an air hole formed in the frame body to guide air introduced from an outside into a space between the frame body and the proximal balloon.

6. The colon linearizing device of claim 5, wherein the proximal frame further comprises a wire hole formed through the frame body.

7. A method of manufacturing the colon linearizing device set forth in claim 1,
wherein at least one of the distal member and the proximal member comprises:
a frame having a hollow for receiving the insertion tube; and
a balloon disposed with both ends in close contact with an outer circumferential surface of the frame and formed of a flexible material,
wherein the method comprises:
manufacturing a mold corresponding to an outer shape of the balloon;
forming the balloon by injecting silicone in the mold and curing the silicone;
installing the balloon on a side surface of the frame and fixing both ends of the balloon to the side surface of the frame; and
installing an air tube capable of supplying air from an outside to a space between the frame and the balloon.

8. The method of claim 7, wherein the balloon is capable of expanding in a direction toward an outside diameter of the frame and incapable of expanding in a direction toward an inside diameter of the frame.

9. A colon linearizing device installed in an endoscope to linearize a colon by performing translation and expansion motions in the colon, the colon linearizing device comprising:
a ring-shaped proximal member installed to surround an outer circumferential surface of an insertion tube of an endoscope;
a fixed end secured to the insertion tube;
a ring-shaped distal member positioned between the proximal member and the fixed end and movably installed along a longitudinal direction of the insertion tube;

an elastic member connected between the fixed end and the distal member;

a translation drive device to translate the distal member, wherein the translation drive device includes a base and a driving block capable of sliding relative to the base; and an expansion drive device to expand the distal member or the proximal member by supplying air pressure to the distal member or the proximal member, wherein the expansion drive device includes an air tube, wherein the translation drive device further comprises:

a vertically moving block capable of sliding relative to the base and connected to the distal member; and an electromagnet module capable of magnetically coupling the driving block and the vertically moving block.

10. The colon linearizing system of claim 9, wherein the electromagnet module comprises:

a first magnetic body installed in any one of the driving block and the vertically moving block; and a second magnetic body installed in the other one of the driving block and the vertically moving block.

11. The colon linearizing system of claim 9, wherein the translation drive device further comprises:

a driving motor; and a drive shaft to rotate according to an operation of the driving motor and translate the driving block in a ball-screw manner.

12. The colon linearizing system of claim 9, wherein the expansion drive device comprises:

the air tube to supply air pressure to the distal member or the proximal member;

an air pressure sensor to measure pressure in the air tube; and an air pressure controller to control the pressure in the air tube according to an input time and pressure conditions.

\* \* \* \* \*